(12) United States Patent
Yamada

(10) Patent No.: US 10,375,960 B2
(45) Date of Patent: Aug. 13, 2019

(54) RESIN COMPOSITION INCLUDING INSECTICIDAL COMPONENT

(71) Applicant: Innovative Vector Control Consortium, Liverpool, Merseyside (GB)

(72) Inventor: Noriko Yamada, Takarazuka (JP)

(73) Assignee: INNOVATIVE VECTOR CONTROL CONSORTIUM, Liverpool, Merseyside (GB)

( * ) Notice: Subject to any disclaimer, the term of this patent is extended or adjusted under 35 U.S.C. 154(b) by 0 days.

(21) Appl. No.: 15/761,787

(22) PCT Filed: Sep. 23, 2016

(86) PCT No.: PCT/JP2016/077942
§ 371 (c)(1),
(2) Date: Mar. 20, 2018

(87) PCT Pub. No.: WO2017/051840
PCT Pub. Date: Mar. 30, 2017

(65) Prior Publication Data
US 2018/0255778 A1    Sep. 13, 2018

(30) Foreign Application Priority Data

Sep. 25, 2015  (JP) .................................. 2015-187869
Mar. 17, 2016  (JP) .................................. 2016-053441

(51) Int. Cl.
| | | |
|---|---|---|
| *A01N 43/54* | (2006.01) |
| *A01N 25/10* | (2006.01) |
| *A01N 25/34* | (2006.01) |
| *C08K 5/3462* | (2006.01) |
| *C08L 23/06* | (2006.01) |
| *A47C 29/00* | (2006.01) |
| *A01M 1/20* | (2006.01) |
| *A01M 29/34* | (2011.01) |
| *D01F 1/10* | (2006.01) |
| *D01F 6/04* | (2006.01) |

(52) U.S. Cl.
CPC ........... *A01N 43/54* (2013.01); *A01M 1/2055* (2013.01); *A01M 29/34* (2013.01); *A01N 25/10* (2013.01); *A01N 25/34* (2013.01); *A47C 29/006* (2013.01); *C08K 5/3462* (2013.01); *C08L 23/06* (2013.01); *D01F 1/10* (2013.01); *D01F 6/04* (2013.01)

(58) Field of Classification Search
CPC ......... C08L 23/08; A01N 25/34; A01N 25/10; A01M 1/2055; A01M 29/34
See application file for complete search history.

(56) References Cited

U.S. PATENT DOCUMENTS 9,725,418 B2 *  8/2017  Uneme ................ C07D 239/42

FOREIGN PATENT DOCUMENTS

JP    WO 2015/146870    * 10/2015

* cited by examiner

*Primary Examiner* — Johann R Richter
*Assistant Examiner* — Danielle D Sullivan
(74) *Attorney, Agent, or Firm* — Foley & Lardner LLP

(57) ABSTRACT

The present invention provides: a resin composition which includes a polyethylene resin, and 5-chloro-4-ethyl-6-[2-(4-trifluoromethylphenyl)ethylamino]pyrimidine; an insect pest control material obtained by causing the 5-chloro-4-ethyl-6-[2-(4-trifluoromethylphenyl)ethylamino]pyrimidine to be held on the polyethylene resin; and a pest control method provided with a step in which the insect pest control material is placed in the habitat of a pest.

8 Claims, 1 Drawing Sheet

RESIN COMPOSITION INCLUDING INSECTICIDAL COMPONENT

RELATED APPLICATIONS

The present application claims priority under 37 U.S.C. § 371 to International Patent Application No. PCT/JP2016/077942, filed Sep. 23, 2016, which claims priority to and the benefit of Japanese Patent Application Nos. 2015-187869 filed on Sep. 25, 2015 and 2016-053441 filed on Mar. 17, 2016. The contents of these applications are hereby incorporated by reference in their entireties.

TECHNICAL FIELD

The present invention relates to a resin composition comprising an insecticidal ingredient.

BACKGROUND ART

A controlling material formed by processing a resin composition comprising an insecticidal ingredient into a sheet or a net is widely used to control pests. For example, Patent Document 1 describes a resin composition comprising pyrethroid as an insecticidal ingredient, and a pest controlling material formed by processing the resign composition. These compositions and materials however do not have sufficient performance, and it has been thus desired to provide a resin composition and a pest controlling material each having an excellent control efficacy against pests.

CITATION LIST

Patent Document

Patent Document 1: Japanese Laid-Open Patent Publication No. 8-302080

SUMMARY OF THE INVENTION

Problems to be Solved by Invention

An object of the present invention is to provide a resin composition and a pest controlling material, each having an excellent control efficacy against pests.

Means to Solve Problems

The present inventor has intensively studied to achieve the object and, as a result, found out that a resin composition comprising a polyethylene resin and 5-chloro-4-ethyl-6-[2-(4-trifluoromethylphenyl)ethylamino]pyrimidine as an insecticidal ingredient, and a pest control material which is formed by retaining 5-chloro-4-ethyl-6-[2-(4-trifluoromethylphenyl)ethylamino]pyrimidine into the polyethylene resin each has an excellent pest control efficacy, and thus the inventor achieved the present invention. That is, the present invention is as follows.

[1] A resin composition comprising a polyethylene resin and 5-chloro-4-ethyl-6-[2-(4-trifluoromethylphenyl)ethylamino]pyrimidine.

[2] The resin composition according to [1], wherein a weight ratio of 5-chloro-4-ethyl-6-[2-(4-trifluoromethylphenyl)ethylamino]pyrimidine to the polyethylene resin is within the range of 0.1 to 25 parts by weight relative to 100 parts by weight of the polyethylene resin.

[3] A pest control material which is formed by retaining 5-chloro-4-ethyl-6-[2-(4-trifluoromethylphenyl)ethylamino]pyrimidine into the polyethylene resin.

[4] The pest control material according to [3], wherein the material is in a filament form.

[5] The pest control material according to [3], wherein the material is in a net form.

[6] The pest control material according to [3], wherein the material is in a mosquito bed net form.

[7] The pest control material according to any one of [3] to [6], wherein the material is a resin molded body which is made from the resin composition according to [1] or [2].

[8] A method for controlling pests comprising placing the pest control material according to any one of [3] to [7] in habitat of the pests.

According to the present invention, a resin composition and a pest control material each having an excellent pest control efficacy can be provided.

BRIEF DESCRIPTION OF DRAWING(S)

EMBODIMENT FOR CARRYING OUT THE INVENTION

Figure 1:
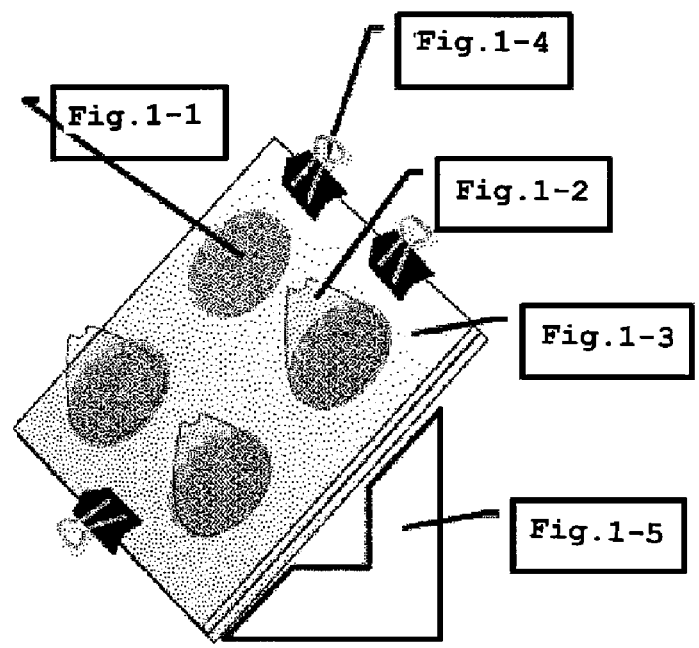
FIG. 1 represents a diagram of an overview of a testing method of Test Example 2.

The resin composition of the present invention (hereinafter, referred to as "resin composition of the present invention") comprises a polyethylene resin and 5-chloro-4-ethyl-6-[2-(4-trifluoromethylphenyl)ethylamino]pyrimidine (hereinafter, referred to as "the present compound") as an insecticidal ingredient. The present compound can be prepared, for example, by a method described in <Preparation Example 1> herein.

Examples of the polyethylene resin used herein include polyethylene resins such as a low density polyethylene (including linear low density polyethylene (LLDPE)), an ultra-low density polyethylene, a medium density polyethylene, a high density polyethylene, and copolymers composed of ethylene and α-olefin having 3 or more carbon atoms; and copolymers composed of a carboxylic acid derivative having an ethylenically unsaturated bond and ethylene such as an ethylene-methyl methacrylate copolymer, an ethylene-vinyl acetate copolymer, and an ethylene-acrylic acid copolymer each singly or any combination of two or more thereof, but are not limited thereto. Examples of such a polyethylene resin include the low density polyethylene and the linear low density polyethylene each having a density of 0.85 to 0.93 g/cm$^3$, and the high density polyethylene having a density of 0.94 g/cm$^3$ or more.

The resin composition of the present invention comprises, preferably, 0.1 to 25 parts by weight and, more preferably, 0.1 to 9.0 parts by weight of the present compound relative to 100 parts by weight of the polyethylene resin.

The resin composition of the present invention may optionally comprise one or more of the following solvents aiming at imparting the dispersibility and the fluidity to the insecticidal ingredient. Examples of the solvent include saturated hydrocarbons having 10 to 20 carbon atoms; paraffin-based solvents such as n-paraffin, isoparaffin, cycloparaffin, and liquid paraffin; aromatic system solvents such as xylene, alkylbenzene, alkylnaphthalene, phenyl xylyl ethane, and diphenyl xylylethane; ketones such as cyclohexanone, heptanone, octanone, nonanone, or acetophenone; esters such as hexyl acetate, benzyl acetate, phenylethyl acetate, benzyl benzoate, methyl benzoate, isobutyl oleate, benzyl salicylate, butylcyclohexyl acetate, methylbenzyl acetate, methyl oleate, methyl laurate, isopropyl myristate, isopropyl palmitate, isononyl isononanoate, and octyl palmitate; cyclic carbonates such as 1,2-butylene carbonate and propylene carbonate; cyclic amides such as N-dodecyl pyrolidone and N-octyl pyrolidone; cyclic urea such as 1,3-dimethyl-2-imidazolidinone; higher fatty carboxylic acids such as linoleic acid and palmitic acid; alcohols such as ethyleneglycol, propylene glycol, benzyl alcohol, phenylethyl alcohol, and polyethylene glycol; plant oils such as canola oil, soy oil, flax seed oil, olive oil, and rice bran oil.

The resin composition of the present invention may optionally comprise one or more of the following porous powder carriers aiming at imparting the slow release property to the insecticidal ingredient. Examples of the porous powder carrier include silica, diatom earth, aluminum oxide, titanium oxide, iron oxide, zinc oxide, glass beads, zeolite, calcium carbonate, zinc carbonate, barium carbonate, mica, barium sulfate, talc, kaolin, clay, silica-based fine particles, activated carbon, and dextrin. The average particle diameter of the porous powder carrier generally is, preferably, within the range from 0.01 to 40 μm and is, more preferably, within the range from 0.03 to 20 μm.

In addition to the above components, it is reasonable that if necessary, the resin composition of the present invention may be optionally added with an antioxidant such as dibutylhydroxytoluene (hereinafter, referred to as "BHT"), a smoothing agent such as zinc stearate, and a compounding agent such as a pigment.

The resin composition of the present invention can be obtained as a resin composition in a powder form, a sheet form, or a pellet form by mixing the polyethylene resin, the present compound, and optionally the other components using a mixer such as a Banbury mixer, a super mixer, and an extruder to obtain a kneaded substance, and if necessary, molding and/or processing the kneaded substance using a pressurizing pressing machine and/or a pelletizer or the like.

The pest control material of the present invention is formed by retaining the present compound into the polyethylene resin. The pest control material of the present invention may be, for example, a resin molded body formed by molding with the resin composition of the present invention (hereinafter, referred to as "the present resin molded body"). Examples of the pest control material of the present invention include the resin molded bodies processed into, for example, a wallpaper sheet, an insecticidal sheet for construction materials, a tape, a banner, a reed screen, a curtain, a mosquito bed net, a screen, a suspended-type item, a strip, or a net. The resin molded body is manufactured after undergoing the ordinary resin processing steps such as mold injection processing, blow-mold processing, extrusion processing, sheet processing, film processing, or knitting processing after the fiber spinning using the resin composition of the present invention.

A method of obtaining the present resin molded body using sheet processing is described. For example, when stretching processing is applied, a biaxial stretching method is usually used. Examples of the method include a sequential biaxial stretching method and a simultaneous biaxial stretching method based on a flat die method, and a tubular (bubble) method based on a circular die method, and among them, the flat die method showing an excellent thickness uniformity of the sheet is advantageously used.

A preparation method using the sequential biaxial stretching method is described.

First, the resin composition in pellets form is led into an extruder and is melted and kneaded therein to make a uniformly melted substance. The substance is then passed through a polymer filter to remove contaminants and the others, and a sheet is thereafter formed.

The resulting sheet is led onto a cooling drum, is adhered tightly thereto with a pressurized air, and is solidified while cooling. In the procedure, the sufficient cooling is preferably carried out to reduce the stretching tension during the subsequent stretching, resulting in obtaining a uniform sheet. Various cooling means can be taken, and include, for example, a method of cooling the sheet by leading it into a water tank immediately after adhering the sheet to the cooling drum, and a method of cooling the sheet surface on the air side by applying a water in a mist form.

Also, examples of specific forms of the present resin molded body include a monofilament and a multifilament. Using the filament, filament products having the insecticidal performance, such as clothes, household commodities, daily goods, outdoor products, articles for agriculture, forestry, and fishery, and sanitary goods can be molded.

The monofilament is a continuous fiber made from one single fiber. In general, the monofilament is produced by cooling and stretching each one of yarns melted and extruded from several 10 to several hundred fiber spinning nozzles present in one die, and collecting the cooled and stretched yarns.

The cross-sectional shape of the monofilament is not particularly limited, and the monofilament may have any cross-sectional shape such as a circle, a hollo shape, a flattened shape, a square, a half-moon shape, a triangle, or a polygon having 5 or more sides. A complex monofilament such as those of a core-clad type and a sea-island type may be used. The monofilament used herein is preferably that of 50 to 1,000 deniers, and the type thereof can properly be selected depending on the use thereof.

A multifilament is one fiber formed by twisting together several to several 10 filaments and is used for ropes, nets, pile materials of carpets, original yarns for unwoven fabric, and the like.

An example of the preparation method of the multifilament is described as follows. First, many yarns discharged from the fiber spinning nozzle are cooled by passing them through a cooling zone. This cooling may be carried out to such an extent that the yarns are not fusion-bonded to each other. After the cooling, an oil agent is applied to the yarns with an oiling roller. After rolling up the yarns or at a subsequent stretching step, the yarns are twisted (drafting) and are collected.

The multifilament used herein is preferably that of 50 to 500 deniers formed by twisting single filaments of 1 to 100 denier(s), and the type thereof can properly be selected depending on the use thereof.

The filaments formed by molding the resin composition of the present invention are knitted, woven, or thermally fusion-bonded with each other, and is preferably used in the net form. The net can be used as it is as a flat knitted fabric in the net form, or can be used as, for example, a mosquito bed net and the like by undergoing a sewing process.

Examples of the shape of the mosquito bed net include a mosquito bed nets formed by sewing the fabric into a square pole or a trapezoidal cone, and advantageously, any ideas are applied to the mosquito bed net to acquire a shape easy to use depending on the size of the room or the size of the bed. The mosquito bed net is installed by being suspended from the ceiling, or by being suspended from the walls using hooks that are driven into the walls. The mosquito bed net is usually used in the manner of covering the room or the bed only during the sleep hours, however, may be used all the day without any problem as long as the mosquito bed net does not make an obstruct. When the pest control material of the present invention is used as a mosquito bed net, an infectious diseases (such as malaria)-vector mosquito contacts with the present compound present on the surface of the filament, and an insecticidal effect and a blood-sucking inhibiting effect can be thereby exerted. The malaria-vector mosquito is nocturnally active and starts its blood-sucking activity when people fall asleep at night.

Thus, in the case where the mosquito tries to approach a person while seeking a source to suck blood, if the person is asleep in the mosquito bed net, the mosquito touches the mosquito bed net before approaching the person, and as a result, the mosquito is efficiently brought into contact with the present compound. The mosquito tormentedly dies or loses its motivation to suck blood by being brought into contact with the present compound. Also, since the present compound is contained in the filaments by kneading the present compound therein, no more ingredients than a necessary amount is not drifted in the room, and the residual efficacy for a prolonged period can also be expected.

The method for controlling pests of the present invention comprises placing the pest control material of the present invention in habitat of the pests, especially, in the vicinity of an inducing source such as a human being or an animal, and when the pest tries to approach the inducing source, the pest is brought into contact with the pest control material of the present invention, and as a result, an insecticidal effect and a blood-sucking inhibiting effect of the present compound retained in the pest control material can control the pests. Also a use as a trap of the pest control material in combination with the inducing sources such as a bait, a heat source, and a light source can control the pests.

Examples of the pests that can be controlled by the pest control material of the present invention include House mosquitoes (Culex spp.) such as common house mosquitoes (Culex pipiens pallens), southern house mosquito (Culex quinquefasciatus), London underground mosquito (Culex pipiens f. molestus), and small size common house mosquito (Culex tritaeniorhynchus); Mosquito-eating mosquitoes (Lutzia spp.) such as Lutzia vorax (Culex halifaxii); Striped mosquitoes (Aedes spp.) such as Asian tiger mosquito (Aedes albopictus), yellow fever mosquito (Aedes aegypti), Mosquito larva (Aedes togoi), Vexans mosquito (Aedes vexans nipponii), Ochlerotatus dorsalis (Aedes dorsalis), and Armigeres subalbatus; Biting midges (Ceratopogonidae spp.) such as Mansonia uniformis; Tripteroides spp. such as Tripteroides bambusa; Anopheles spp. such as Cancer Vieja Madara mosquito (Anopheles gambiae), Chinese anopheles (Anopheles sinensis), and malaria mosquito (Anopheles minimus); Non-biting midges (Chironomidae spp.) such as Chironomus yoshimatsui, chironomus plumosus, Propsilocerus akamusi, striped chironomid, Oyama Chibi midges (Tanytarsus); Horseflies (Tabanus spp.); Flies (Diptera spp.); Black flies (Simulium spp.); Sandflies (Phlebotominae spp.); Biting midges (Ceratopogonidae spp.); Tsetse flies (Glossinidae spp.); Fleas (Ctenocephalides spp.); Louces (Phthiraptera spp.); Bed bugs (Cimex lectularius spp.); Assassin bugs (Triatoma spp.); Cockroaches (blattodea spp.); Ants (Formicidae spp.); Termites (Isoptera spp.); Mites (Acari spp.); Ixodides (Ixodes spp.).

EXAMPLES

The present invention is described in more detail below with reference to Preparation Examples and Test Examples, but the present invention should not be limited thereto.

First, the Preparation Examples are described below.

Preparation Example 1

To a mixture of 2.00 g (10.57 mmol) of [2-(4-trifluoromethylphenyl)ethylamine and 20 ml of DMF were added 2.92 g (21.13 mmol) of potassium carbonate and 2.06 g (11.63 mmol) of 4,5-dichloro-6-ethylpyrimidine, and the reaction mixture was stirred for 5 hours at 90° C. After cooling to room temperature, 60 ml of water was added thereto, and the mixture was extracted three times with ethyl acetate. The organic layer was washed with water and brine, and dried over anhydrous sodium sulfate, and was then concentrated. The residue was subjected to a silica gel column chromatography to give 5-chloro-4-ethyl-6-[2-(4-trifluoromethylphenyl)ethylamino]pyrimidine (the present compound) 3.00 g.

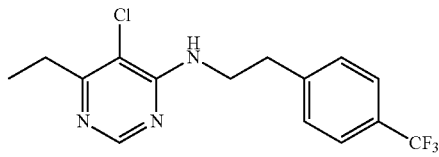 [SMILES: CCc1ncnc(NCCc2ccc(C(F)(F)F)cc2)c1Cl]

$^1$H-NMR (CDCl$_3$) δ: 1.27 (3H, t, J=7.5 Hz), 2.79 (2H, q, J=7.5 Hz), 3.00 (2H, t, J=7.0 Hz), 3.79 (2H, q, J=7.0 Hz), 5.42 (1H, bs), 7.35 (2H, d, J=7.9 Hz), 7.58 (2H, d, J=7.9 Hz), 8.45 (1H, s).

Preparation Example 2

(1) Preparation Method of Resin Composition A

Thirty-four point zero eight (34.08) g of polyethylene having a density of 0.954 g/cm$^3$ and a melt flow rate of 0.95 g/10 min (190° C., 2.16 kg), 0.10 g of silica, 0.46 g of zinc stearate, and 0.19 g of a pigment were put in a Labo Plastomill of a model 4C-150-01 manufactured by Toyo Seiki Seisaku-Sho Ltd., whose mixer temperature was set at 190° C. and whose screw rotation speed was set at 15 rpm. The screw rotation speed thereafter was increased to 50 rpm, and the mixture was then mixed and kneaded for 3 minutes. The screw rotation speed was again set at 15 rpm, and 0.18 g of the present compound was put therein. The screw rotation speed was thereafter increased to 50 rpm and the mixture was mixed and kneaded for 5 minutes to obtain a resin composition A.

(2) Preparation Method of Resin Sheet A

The above resin composition A was sandwiched between metal plates, and was pressed using a compression molding machine AYSR-5 manufactured by Shinto Metal Industries Corporation whose upper and lower pressing plates were heated to 150° C., to obtain a resin sheet A.

Preparation Example 3

(1) Mixing Method of the Present Compound and Additive Solvent to Prepare Mixture B Zero point one eight (0.18) g of the present compound and 0.89 g of propylene carbonate were weighed in a sample bottle (of capacity of 1.8 ml), and thereafter were mixed with each other, and the sample bottle was sealed with a lid. The sample bottle was put in a waterproof pouch with a fastener, and then was warmed in a water bath at 98° C. or higher for 15 minutes. The sample bottle was thereafter shaken up and down to mix its contents to obtain a mixture B of the present compound and an additive solvent.

(2) Preparation Method of Resin Composition B

Thirty two point seven two (32.72) g of polyethylene having a density of 0.954 g/cm$^3$ and a melt flow rate of 0.95 g/10 min (190° C., 2.16 kg), 0.58 g of silica, 0.46 g of zinc stearate, and 0.19 g of a pigment were put in a Labo Plastomill of a model 40-150-01 manufactured by Toyo Seiki Seisaku-Sho Ltd., whose mixer temperature was set at 190° C. and whose screw rotation speed was set at 15 rpm. The screw rotation speed thereafter was increased to 50 rpm, and the mixture was then mixed and kneaded for 3 minutes. The screw rotation speed was again set at 15 rpm, and the mixture B of the present compound and an additive solvent was put therein. The screw rotation speed was thereafter increased to 50 rpm and the mixture was mixed and kneaded for 5 minutes to obtain a resin composition B.

(3) Preparation Method of Resin Sheet B

The above resin composition B was sandwiched between metal plates, and was pressed using a compression molding machine AYSR-5 manufactured by Shinto Metal Industries Corporation whose upper and lower pressing plates were heated at 150° C., to obtain a resin sheet B.

Preparation Example 4

(1) Mixing Method of the Present Compound and Additive Solvent to Prepare Mixture C Zero point one eight (0.18) g of the present compound and 0.88 g of N-dodecylpyrolidone were weighed in a sample bottle (of capacity of 1.8 ml), and thereafter were mixed with each other, and the sample bottle was sealed with a lid. The sample bottle was put in a waterproof pouch with a fastener, and then was warmed in a water bath at 98° C. or higher for 15 minutes. The sample bottle was thereafter shaken up and down to mix its contents to obtain a mixture C of the present compound and an additive solvent.

(2) Preparation Method of Resin Composition C

Thirty two point seven three (32.73) g of polyethylene having a density of 0.954 g/cm$^3$ and a melt flow rate of 0.95 g/10 min (190° C., 2.16 kg), 0.58 g of silica, 0.46 g of zinc stearate, and 0.19 g of a pigment were put in a Labo Plastomill of a model 4C-150-01 manufactured by Toyo Seiki Seisaku-Sho Ltd., whose mixer temperature was set at 190° C. and whose screw rotation speed was set at 15 rpm. The screw rotation speed thereafter was increased to 50 rpm, and the mixture was then mixed and kneaded for 3 minutes. The screw rotation speed was again set at 15 rpm, and the mixture C of the present compound and an additive solvent was put therein. The screw rotation speed was thereafter increased to 50 rpm and the mixture was mixed and kneaded for 5 minutes to obtain a resin composition C.

(3) Preparation Method of Resin Sheet C

The above resin composition C was sandwiched between metal plates, and was pressed using a compression molding machine AYSR-5 manufactured by Shinto Metal Industries Corporation whose upper and lower pressing plates were heated at 150° C., to obtain a resin sheet C.

Preparation Example 5

(1) Mixing Method of the Present Compound and Additive Solvent to Prepare Mixture D Zero point one eight (0.18) g of the present compound and 0.89 g of linoleic acid were weighed in a sample bottle (of capacity of 1.8 ml), and thereafter were mixed with each other, and the sample bottle was sealed with a lid. The sample bottle was put in a waterproof pouch with a fastener, and then was warmed in a water bath at 98° C. or higher for 15 minutes. The sample bottle was thereafter shaken up and down to mix its contents to obtain a mixture D of the present compound and an additive solvent.

(2) Preparation Method of Resin Composition D

Thirty two point seven two (32.72) g of polyethylene having a density of 0.954 g/cm$^3$ and a melt flow rate of 0.95 g/10 min (190° C., 2.16 kg), 0.58 g of silica, 0.46 g of zinc stearate, and 0.19 g of a pigment were put in a Labo Plastomill of a model 4C-150-01 manufactured by Toyo Seiki Seisaku-Sho Ltd., whose mixer temperature was set at 190° C. and whose screw rotation speed was set at 15 rpm. The screw rotation speed thereafter was increased to 50 rpm, and the mixture was then mixed and kneaded for 3 minutes. The screw rotation speed was again set at 15 rpm, and the mixture D of the present compound and an additive solvent was put therein. The screw rotation speed was thereafter increased to 50 rpm and the mixture was mixed and kneaded for 5 minutes to obtain a resin composition D.

(3) Preparation Method of Resin Sheet D

The above resin composition D was sandwiched between metal plates, and was pressed using a compression molding machine AYSR-5 manufactured by Shinto Metal Industries Corporation whose upper and lower pressing plates were heated at 150° C., to obtain a resin sheet D.

Preparation Example 6

(1) Preparation Method of Resin Composition E

Thirty three point two five (33.25) g of polyethylene having a density of 0.954 g/cm$^3$ and a melt flow rate of 0.95 g/10 min (190° C., 2.16 kg), 0.39 g of silica, 0.46 g of zinc stearate, and 0.19 g of a pigment were put in a Labo Plastomill of a model 4C-150-01 manufactured by Toyo Seiki Seisaku-Sho Ltd., whose mixer temperature was set at 190° C. and whose screw rotation speed was set at 15 rpm. The screw rotation speed thereafter was increased to 50 rpm, and the mixture was then mixed and kneaded for 3 minutes. The screw rotation speed was again set at 15 rpm, and 0.70 g of ethofenprox was put therein. The screw rotation speed was thereafter increased to 50 rpm, and the mixture was mixed and kneaded at the screw rotation speed of 15 rpm for 5 minutes to obtain a resin composition E.

(2) Preparation Method of Resin Sheet E

The above resin composition E was sandwiched between metal plates, and was pressed using a compression molding machine AYSR-5 manufactured by Shinto Metal Industries Corporation whose upper and lower pressing plates were heated at 150° C., to obtain a resin sheet E.

Preparation Example 7

(1) Preparation Method of Resin Composition F

Thirty four point three five (34.35) g of polyethylene having a density of 0.954 g/cm$^3$ and a melt flow rate of 0.95 g/10 min (190° C., 2.16 kg), 0.46 g of zinc stearate, and 0.19 g of a pigment were put in a Labo Plastomill of a model 4C-150-01 manufactured by Toyo Seiki Seisaku-Sho Ltd., whose mixer temperature was set at 190° C. and whose screw rotation speed was set at 15 rpm. The screw rotation speed thereafter was increased to 50 rpm, and the mixture was then mixed and kneaded for 8 minutes to obtain a resin composition F.

(2) Preparation Method of Resin Sheet F

The above resin composition F was sandwiched between metal plates, and was pressed using a compression molding machine AYSR-5 manufactured by Shinto Metal Industries Corporation whose upper and lower pressing plates were heated at 150° C., to obtain a resin sheet F.

Preparation Example 8

(1) Preparation Method of Resin Composition G

Forty four point four two (44.42 g) of polyethylene having a density of 0.954 g/cm$^3$ and a melt flow rate of 0.95 g/10 min (190° C., 2.16 kg), 0.28 g of silica, 3.25 g of zinc stearate, 1.38 g of a pigment, 0.17 g of BHT, and 0.50 g of the present compound were put in a Labo Plastomill of a model 4C-150-01 manufactured by Toyo Seiki Seisaku-Sho Ltd., whose mixer temperature was set at 150° C. and whose screw rotation speed was set at 15 rpm. The screw rotation speed thereafter was increased to 30 rpm, and the mixture was then mixed and kneaded for 5 minutes to obtain a resin composition G.

(2) Preparation Method of Resin Sheet G

The above resin composition G was sandwiched between metal plates and was pressed using a compression molding machine AYSR-5 manufactured by Shinto Metal Industries Corporation whose upper and lower pressing plates were heated at 150° C., to obtain a resin sheet G.

(3) Preparation Method of Resin Pellet G

The resin sheet G was cut into strips using a paper cutter and was thereafter cut into particles using a pelletizer of a model NS-III manufactured by Tanabe Plastics Machine Co., Ltd., to obtain resin pellets G.

(4) Preparation Method of Resin Filament G

Fifty point zero zero (50.00) g of the above resin pellets G and 200.00 g of polyethylene having a density of 0.954 g/cm$^3$ and a melt flow rate of 0.95 g/10 min (190° C., 2.16 kg) were mixed with each other, and were put into a melt spinning machine manufactured by Musashino Kikai Co., Ltd., whose extrusion temperature was set at 190° C. and whose screw rotation speed was set at 10 rpm, to obtain resin filaments G of 200 deniers.

(5) Preparation Method of Resin Net G

A resin net G was obtained from the above resin filaments G with a stockinette knitting machine.

Preparation Example 9

(1) Preparation Method of Resin Composition H

Forty three point two six (43.26 g) of polyethylene having a density of 0.917 g/cm$^3$ and a melt flow rate of 20.0 g/10 min (190° C., 2.16 kg), 0.69 g of silica, 3.25 g of zinc stearate, 1.38 g of a pigment, 0.17 g of BHT, and 1.25 g of the present compound were put in a Labo Plastomill of a model 4C-150-01 manufactured by Toyo Seiki Seisaku-Sho Ltd., whose mixer temperature was set at 120° C. and whose screw rotation speed was set at 15 rpm. The screw rotation speed thereafter was increased to 30 rpm, and the mixture was then mixed and kneaded for 5 minutes to obtain a resin composition H.

(2) Preparation Method of Resin Sheet H

The above resin composition H was sandwiched between metal plates and was pressed using a compression molding machine AYSR-5 manufactured by Shinto Metal Industries Corporation whose upper and lower pressing plates were heated at 120° C., to obtain a resin sheet H.

(3) Preparation Method of Resin Pellet H

The above resin sheet H was cut into strips using a paper cutter and was thereafter cut into particles using a pelletizer of a model NS-III manufactured by Tanabe Plastics Machine Co., Ltd., to obtain resin pellets H.

(4) Preparation Method of Resin Filament H

Fifty point zero zero (50.00) g of the above resin pellets H and 200.00 g of polyethylene having a density of 0.954 g/cm$^3$ and a melt flow rate of 0.95 g/10 min (190° C., 2.16 kg) were mixed with each other, and were put into a melt spinning machine manufactured by Musashino Kikai Co., Ltd., whose extrusion temperature was set at 190° C. and whose screw rotation speed was set at 10 rpm, to obtain resin filaments H of 200 deniers.

(5) Preparation Method of Resin Net H

A resin net H was obtained from the above resin filaments H using a stockinette knitting machine.

Preparation Example 10

(1) Mixing Method of the Present Compound and Additive Solvent to Prepare Mixture I One point two five (1.25) g of the present compound and 6.25 g of liquid paraffin were weighed in a sample bottle (of capacity of 20 ml), and thereafter were mixed with each other, and the sample bottle was sealed with a lid. The sample bottle was put in a waterproof pouch with a fastener, and then was warmed in a water bath at 98° C. or higher for 15 minutes. The sample bottle was thereafter shaken up and down to mix its contents to obtain a mixture I of the present compound and an additive solvent.

(2) Preparation Method of Resin Composition I

Thirty three point five eight (33.58 g) of polyethylene having a density of 0.954 g/cm$^3$ and a melt flow rate of 0.95 g/10 min (190° C., 2.16 kg), 4.12 g of silica, 3.25 g of zinc stearate, 1.38 g of a pigment, 0.17 g of BHT, and 7.50 g of the above mixture I were put in a Labo Plastomill of a model R-60H manufactured by Toyo Seiki Seisaku-Sho Ltd., whose mixer temperature was set at 150° C. and whose screw rotation speed was set at 15 rpm. The screw rotation speed thereafter was increased to 30 rpm, and the mixture was then mixed and kneaded for 5 minutes to obtain a resin composition I.

(3) Preparation Method of Resin Sheet I

The above resin composition I was sandwiched between metal plates and was pressed using a compression molding machine AYSR-5 manufactured by Shinto Metal Industries Corporation whose upper and lower pressing plates were heated at 150° C., to obtain a resin sheet I.

(4) Preparation Method of Resin Pellet I

The above resin sheet I was cut into strips using a paper cutter and was thereafter cut into particles using a pelletizer of a model NS-III manufactured by Tanabe Plastics Machinery Co., Ltd., to obtain resin pellets I.

(5) Preparation Method of Resin Filament I

Fifty point zero zero (50.00) g of the above resin pellets I and 200.00 g of polyethylene having a density of 0.954 g/cm$^3$ and a melt flow rate of 0.95 g/10 min (190° C., 2.16 kg) were mixed with each other, and were put into a melt spinning machine manufactured by Musashino Kikai Co., Ltd., whose extrusion temperature was set at 190° C. and whose screw rotation speed was set at 10 rpm, to obtain resin filaments I of 240 deniers.

(6) Preparation Method of Resin Net I

A resin net I was obtained from the above resin filaments I using a stockinette knitting machine.

Preparation Example 11

(1) Preparation Method of Resin Composition J

Thirty seven point four five (37.45 g) of polyethylene having a density of 0.954 g/cm$^3$ and a melt flow rate of 0.95 g/10 min (190° C., 2.16 kg), 2.75 g of silica, 3.25 g of zinc stearate, 1.38 g of a pigment, 0.17 g of BHT, and 5.00 g of the present compound were put in a Labo Plastomill of a model R-60H manufactured by Toyo Seiki Seisaku-Sho Ltd., whose mixer temperature was set at 150° C. and whose screw rotation speed was set at 15 rpm. The screw rotation speed thereafter was increased to 30 rpm, and the mixture was then mixed and kneaded for 5 minutes to obtain a resin composition J.

(2) Preparation Method of Resin Sheet J

The above resin composition J was sandwiched between metal plates and was pressed using a compression molding machine AYSR-5 manufactured by Shinto Metal Industries Corporation whose upper and lower pressing plates were heated at 150° C., to obtain a resin sheet J.

(3) Preparation Method of Resin Pellet J

The above resin sheet J was cut into strips using a paper cutter and was thereafter cut into particles using a pelletizer of a model NS-III manufactured by Tanabe Plastics Machinery Co., Ltd., to obtain resin pellets J.

(4) Preparation Method of Resin Filament J

Fifty point zero zero (50.00) g of the above resin pellets J and 200.00 g of polyethylene having a density of 0.954 g/cm$^3$ and a melt flow rate of 0.95 g/10 min (190° C., 2.16 kg) were mixed with each other, and were put into a melt spinning machine manufactured by Musashino Kikai Co., Ltd., whose extrusion temperature was set at 190° C. and whose screw rotation speed was set at 10 rpm, to obtain resin filaments J of 183 deniers.

(5) Preparation Method of Resin Net J

A resin net J was obtained from the above resin filaments J using a stockinette knitting machine.

Preparation Example 12

(1) Preparation Method of Resin Composition K

Forty four point four two (44.42 g) of polyethylene having a density of 0.954 g/cm$^3$ and a melt flow rate of 0.95 g/10 min (190° C., 2.16 kg), 0.28 g of silica, 3.25 g of zinc stearate, 1.38 g of a pigment, 0.17 g of BHT, and 0.50 g of deltamethrin were put in a Labo Plastomill of a model R-60H manufactured by Toyo Seiki Seisaku-Sho Ltd., whose mixer temperature was set at 150° C. and whose screw rotation speed was set at 15 rpm. The screw rotation speed thereafter was increased to 30 rpm, and the mixture was then mixed and kneaded for 5 minutes to obtain a resin composition K.

(2) Preparation Method of Resin Sheet K

The above resin composition K was sandwiched between metal plates and was pressed using a compression molding machine AYSR-5 manufactured by Shinto Metal Industries Corporation whose upper and lower pressing plates were heated at 150° C., to obtain a resin sheet K.

(3) Preparation Method of Resin Pellet K

The above resin sheet K was cut into strips using a paper cutter and was thereafter cut into particles using a pelletizer of a model NS-III manufactured by Tanabe Plastics Machinery Co., Ltd., to obtain resin pellets K.

(4) Preparation Method of Resin Filament K

Fifty point zero zero (50.00) g of the above resin pellets K and 200.00 g of polyethylene having a density of 0.954 g/cm$^3$ and a melt flow rate of 0.95 g/10 min (190° C., 2.16 kg) were mixed with each other, and were put into a melt spinning machine manufactured by Musashino Kikai Co., Ltd., whose extrusion temperature was set at 190° C. and whose screw rotation speed was set at 10 rpm, to obtain resin filaments K of 200 deniers.

(5) Preparation Method of Resin Net K

A resin net K was obtained from the above resin filaments K using a stockinette knitting machine.

Preparation Example 13

(1) Preparation Method of Resin Composition L

Forty four point nine two (44.92 g) of polyethylene having a density of 0.954 g/cm$^3$ and a melt flow rate of 0.95 g/10 min (190° C., 2.16 kg), 0.28 g of silica, 3.25 g of zinc stearate, 1.38 g of a pigment, and 0.17 g of BHT were put in a Labo Plastomill of a model R-60H manufactured by Toyo Seiki Seisaku-Sho Ltd., whose mixer temperature was set at 150° C. and whose screw rotation speed was set at 15 rpm. The screw rotation speed thereafter was increased to 30 rpm, and the mixture was then mixed and kneaded for 5 minutes to obtain a resin composition L.

(2) Preparation Method of Resin Sheet L

The above resin composition L was sandwiched between metal plates and was pressed using a compression molding machine AYSR-5 manufactured by Shinto Metal Industries Corporation whose upper and lower pressing plates were heated at 150° C., to obtain a resin sheet L.

(3) Preparation Method of Resin Pellet L

The above resin sheet L was cut into strips using a paper cutter and was thereafter cut into particles using a pelletizer of a model NS-III manufactured by Tanabe Plastics Machinery Co., Ltd., to obtain resin pellets L.

(4) Preparation Method of Resin Filament L

Fifty point zero zero (50.00) g of the above resin pellets L and 200.00 g of polyethylene having a density of 0.954 g/cm$^3$ and a melt flow rate of 0.95 g/10 min (190° C., 2.16 kg) were mixed with each other, and were put into a melt spinning machine manufactured by Musashino Kikai Co., Ltd., whose extrusion temperature was set at 190° C. and whose screw rotation speed was set at 10 rpm, to obtain resin filaments L of 200 deniers.

(5) Preparation Method of Resin Net L

A resin net L was obtained from the above resin filaments L using a stockinette knitting machine.

Second, the Test Examples are described below.

Test Example 1

The basic insecticidal activity of the present compound was examined using a topical application method. Various concentrations of acetone solutions of the present compound were previously prepared. A female adult of Cancer Vieja Madara mosquito (*Anopheles gambiae* Kisumu-strain) was treated by dropping via a micro syringe 0.3 μL of the prepared acetone solution to a thoracodorsal region of the mosquito under anesthesia with carbon dioxide gas that did not yet suck any blood. After the treatment, the female adult of Cancer Vieja Madara mosquito was moved into a plastic cup (having a diameter of 9 cm and a height of about 4.5 cm), and was fed with 5% sugar water. The mortality after 24 hours was examined. The number of the tested female adults of Cancer Vieja Madara mosquito was 10 heads per each one concentration in four replicate experiments. The 50% lethal dose (the $LD_{50}$ value) of the present compound was calculated from the test result using probit method. The same experiment was conducted using ethofenprox as a control. The lower 50% lethal dose of a compound means the higher basic insecticidal activity of the compound. The ratio of the $LD_{50}$ value of the present compound relative to the $LD_{50}$ value of ethofenprox was calculated to acquire the relative efficacy of the present compound to ethofenprox. The result thereof is shown in Table 1.

TABLE 1

| Tested Compound | 50% Lethal Dose (LD50) (µg/female) | Relative Efficacy |
| --- | --- | --- |
| The present compound | 0.0094 | 0.22 |
| Ethofenprox | 0.0021 | 1 |

Test Example 2

A 13 cm×13 cm segment (FIG. 1-1) of each of the resin sheets A and E of Preparation Examples 2 and 6 was cut out as a test sample. Each of the segments was adhered to a panel using a double-sided adhesive tape according to a standard WHO cone technique method described in the below-mentioned reference, and a plastic cup (having an upper inner diameter of 3 cm, a lower inner diameter of 9 cm, and a height of 6 cm) having a cone shape (whose upper and lower ends are open) (FIG. 1-2) was mounted thereon. Another panel was put over the cone-shaped cup (FIG. 1-3) and was fixed using clips (FIG. 1-4), and the overall assembly was put on a seating that was oblique by 45 degrees (FIG. 1-5). The female adults of Cancer Vieja Madara mosquito (*Anopheles gambiae* Kisumu-strain) that did not yet suck any blood were blown into the cone-shaped cup from a hole in an upper portion thereof, and were exposed for 15 minutes, and the female adults of Cancer Vieja Madara mosquito unable to stay still on the surface of the cone-shaped cup due to the slipperiness of the surface were brought into contact with the resin sheet. The number of the tested female adults of Cancer Vieja Madara mosquito was 10 heads per each one concentration in two replicate experiments. After the exposure, the female adults of Cancer Vieja Madara mosquito were moved into a plastic cup (having the diameter of 9 cm and a height of about 4.5 cm), and was fed with 5% sugar water. The number of the dead insects 3 days after the exposure was counted to acquire the mortality of the insects after 3 days according to Eq. (a). The higher rate of the mortality of the tormentedly died mosquitoes means the higher insecticidal activity due to a contact. The result is shown in Table 2.

REFERENCE

WHOPES (2005), Guidelines for laboratory and field testing of long-lasting insecticidal mosquito nets, WHO/CDS/WHOPES/GCDPP/2005.11 Geneva, WHO.

Mortality of Insects after 3 Days (%)=Number of Dead Insects after 3 Days/Total Number of tested Insects×100  Eq. (a)

TABLE 2

| Sample | Mortality of Insects after 3 Days (%) |
| --- | --- |
| The resin sheet A | 90.9 |
| The resin sheet E | 42.9 |

Test Example 3

Figure 2:
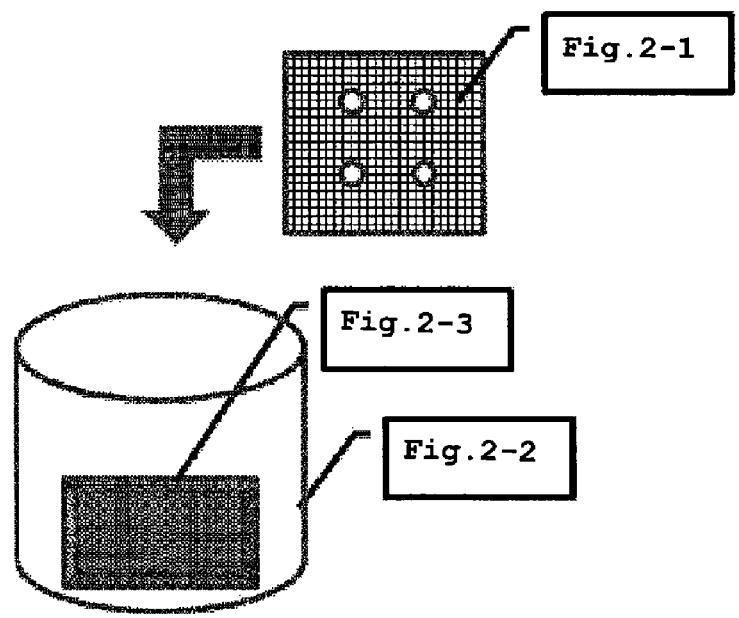
FIG. 2 represents a diagram of an overview of a testing method of Test Example 3.

Four entrance holes (4): 1 cm) for the mosquitoes and 64 ventilation holes (φ: 0.2 cm) were opened in a 13 cm×13 cm segment of each of the resin sheets A and E of Preparation Examples 2 and 6 (FIG. 2-1) and the segment was placed on the upper face of a plastic cup (having a diameter of 12 cm and a height of 10 cm) (FIG. 2-2). An inducing source (FIG. 2-3) was put in the plastic cup and the plastic cup was placed in a cage (21×21×28 cm). Fifty (50) heads of female adults of Cancer Vieja Madara mosquito (*Anopheles gambiae* Kisumu-strain) that did not yet suck any blood were released in the cage at 17:00. Under such an environment, the released female adults of Cancer Vieja Madara mosquito were necessarily brought into contact with the resin sheet that was placed on the upper face of the plastic cup when the released female adults of Cancer Vieja Madara mosquito tried to seek the openings to approach the inducing source. At 9:00 in the next morning, the female adults of Cancer Vieja Madara mosquito in the cage were collected, were moved into a plastic cup (having a diameter of 9 cm, a height of about 4.5 cm), and were fed with 5% sugar water. The number of the dead insects after 24 hours was counted to acquire the mortality of the insects after 24 hours according to Eq. (b). The sample with the higher mortality of the insects after 24 hours means the higher insecticidal activity due to a contact of the sample under the condition of the presence of the inducing source. The result is shown in Table 3.

Mortality of Insects after 24 Hours (%)=Number of Dead Insects after 24 hours/Total Number of tested Insects×100  Eq. (b)

TABLE 3

| Sample | Mortality of Insects after 24 Hours (%) |
| --- | --- |
| The resin sheet A | 100.0 |
| The resin sheet E | 37.3 |

Test Example 4

The basic insecticidal activity of each of the present compound and deltamethrin was examined using the same method as that used in Test Example 1. Here the tested female adults of Cancer Vieja Madara mosquito were pyrethroid-resistive female adults of Cancer Vieja Madara mosquito (*Anopheles gambiae* VK7-strain), and the number of the tested insects was 10 heads per each one concentration in two replicate experiments. The ratio of the $LD_{50}$ value of the present compound relative to the $LD_{50}$ value of deltamethrin was calculated to acquire the relative efficacy of the present compound to deltamethrin. The result thereof is shown in Table 4.

TABLE 4

| Tested Compound | 50% Lethal Dose (LD50) (μg/female) | Relative Efficacy |
| --- | --- | --- |
| The present compound | 0.01833 | 0.05674 |
| Deltamethrin | 0.00104 | 1 |

Test Example 5

The blood sucking inhibiting effect of the resin nets G and K obtained in Preparation Examples 8 and 12 on the pyrethroid-resistive female adults of Cancer Vieja Madara mosquito (*Anopheles gambiae* VK7-strain) was examined according to a standard WHO tunnel method described in the below-mentioned reference. The device used for the standard WHO tunnel method was assembled according to the description in the below-mentioned reference. Specifically, the device was consisted of a glass tunnel portion (having a height of 25 cm, a width of 25 cm, and a length of 60 cm) and cage portions (each having 25-cm sides) connected to both ends of the tunnel portion. Each of the molded products were fixed to a metal frame, and an area of 20 cm×20 cm was exposed, and was placed at a position that was ⅓ from an end of the glass tunnel (namely, 20 cm from the end) to dispose two sections in the tunnel. Nine (9) holes each having a diameter of 1 cm were disposed at 9 points at intervals of 5 cm in each of the resin nets for the mosquitos to pass therethrough. When the mosquitos passed through these holes to move between the sections, the mosquitos necessarily brought into contact with the resin net. An inducing source was placed in a short section of the tunnel, and at 18:00, 110 heads of the pyrethroid-resistive female adults of Cancer Vieja Madara mosquito (*Anopheles gambiae* VK7-strain) each at 3 to 5 days instar larval after an adult eclosion were released in the section that is opposite to the inducing source and is across the tested sample.

After the test came to an end at 9:00 in the next morning, the female adults of Cancer Vieja Madara mosquito were moved into a plastic cup (having a diameter of 9 cm and a height of about 4.5 cm), and the number of blood-sucking insects was counted to acquire the blood-sucking rate according to Eq. (c). The blood-sucking inhibiting rate for the tested sample was calculated according to Eq. (d) that was corrected using the blood-sucking rate of the control sample. A sample with a higher blood-sucking inhibiting rate means a higher blood-sucking inhibiting activity of the sample under the condition of the presence of the inducing source. The control sample was the resin net L. The result is shown in Table 5.

REFERENCE

WHOPES (2005), Guidelines for laboratory and field testing of long-lasting insecticidal mosquito nets, WHO/CDS/WHOPES/GCDPP/2005.11 Geneva, WHO.

$$\text{Blood-Sucking Rate (\%)} = \text{Number of Blood-Sucking Insects/Total Number of tested Insects} \times 100 \quad \text{Eq. (c)}$$

$$\text{Blood-Sucking inhibiting Rate (\%)} = (\text{Blood-Sucking Rate of Control Sample (\%)} - \text{Blood-Sucking Rate of Tested Sample (\%)})/\text{Blood-Sucking Rate of Control Sample (\%)} \times 100 \quad \text{Eq. (d)}$$

TABLE 5

| Sample | Blood-Sucking inhibiting Rate (%) |
| --- | --- |
| The resin net G | 98.8 |
| The resin net K | 39.8 |

The invention claimed is:

1. A resin composition comprising a polyethylene resin and 5-chloro-4-ethyl-6-[2-(4-trifluoromethylphenyl)ethylamino]pyrimidine.

2. The resin composition according to claim 1, wherein a weight ratio of 5-chloro-4-ethyl-6-[2-(4-trifluoromethylphenyl)ethylamino]pyrimidine to the polyethylene resin is within the range of 0.1 to 25 parts by weight relative to 100 parts by weight of the polyethylene resin.

3. A pest control material which is formed by retaining 5-chloro-4-ethyl-6-[2-(4-trifluoromethylphenyl)ethylamino]pyrimidine into a polyethylene resin.

4. The pest control material according to claim 3, wherein the material is in a filament form.

5. The pest control material according to claim 3, wherein the material is in a net form.

6. The pest control material according to claim 3, wherein the material is in a mosquito bed net form.

7. A pest control material wherein the material is a resin molded body which is made from a resin composition comprising a polyethylene resin and 5-chloro-4-ethyl-6-[2-(4-trifluoromethylphenyl)ethylamino]pyrimidine.

8. A method for controlling pests comprising placing the pest control material according to claim 3 in a habitat of the pests.

* * * * *